(12) United States Patent
Merrill et al.

(10) Patent No.: US 7,981,377 B2
(45) Date of Patent: Jul. 19, 2011

(54) DEHYDROGENATION OF ALKYL AROMATICS

(75) Inventors: James Merrill, Morgan, TX (US); Thomas Parenteau, Houston, TX (US); Marcus Ledoux, Baton Rouge, LA (US); Mark Gremillion, Baton Rouge, LA (US)

(73) Assignee: Fina Technology, Inc., Houston, TX (US)

( * ) Notice: Subject to any disclaimer, the term of this patent is extended or adjusted under 35 U.S.C. 154(b) by 604 days.

(21) Appl. No.: 11/982,961

(22) Filed: Nov. 6, 2007

(65) Prior Publication Data

US 2009/0118557 A1    May 7, 2009

(51) Int. Cl.
  *B01J 8/02*    (2006.01)
  *B01J 8/04*    (2006.01)
  *B01J 19/26*   (2006.01)

(52) U.S. Cl. ........ 422/218; 422/636; 422/637; 585/440; 585/441

(58) Field of Classification Search .................. 422/211, 422/218, 630, 631, 636, 637
See application file for complete search history.

(56) References Cited

U.S. PATENT DOCUMENTS

| | | | |
|---|---|---|---|
| 3,719,207 A * | 3/1973 | Takeda | 366/181.5 |
| 3,790,086 A * | 2/1974 | Masai | 239/406 |
| 5,323,661 A | 6/1994 | Cheng | |
| 5,358,698 A | 10/1994 | Butler et al. | |
| 6,096,937 A | 8/2000 | Butler et al. | |
| 6,380,449 B1 | 4/2002 | Butler et al. | |
| 6,686,999 B2 | 2/2004 | Ketkar | |
| 6,727,398 B2 | 4/2004 | Merrill | |
| 6,762,335 B1 | 7/2004 | Prince et al. | |
| 6,781,024 B2 | 8/2004 | Butler et al. | |
| 6,936,743 B2 | 8/2005 | Butler | |
| 2006/0183953 A1* | 8/2006 | Ledoux et al. | 585/444 |

FOREIGN PATENT DOCUMENTS

WO    WO 2007/081781    7/2007

* cited by examiner

*Primary Examiner* — Jennifer A Leung
(74) *Attorney, Agent, or Firm* — Bradley A. Misley

(57) ABSTRACT

Dehydrogenation of a reactor system of one or more vertically oriented flow reactors equipped with a system for introducing a catalyst extender into the inlet of the reactor. A vertically oriented radial flow reactor comprises inner and outer reactor tubes having perforated wall members extending longitudily of the reactor and defining an annulus containing a dehydrogenation catalyst. A supply line to the reactor is equipped with a rotation vane. An injection nozzle comprising a coaxial flow tube extends into the supply line downstream of the vane. The coaxial flow tube has an interior chamber and an annular chamber surrounding the interior chamber and extending into the supply line along with the interior chamber. The interior chamber is connected to a catalyst extender source and the annular chamber is connected to a source of a carrier gas which is effective to disperse the extender within feedstock flowing into the reactor.

15 Claims, 8 Drawing Sheets

DEHYDROGENATION OF ALKYL AROMATICS

FIELD OF INVENTION

This invention relates to the production of vinyl aromatic compounds, such as styrene and more particularly to reactor systems and processes for the dehydrogenation of an alkyl aromatic compound to a corresponding vinyl aromatic compound.

BACKGROUND OF THE INVENTION

Vinyl aromatic compounds such as styrene and methyl styrene are important components in the petrochemical industry which can be employed to produce a wide variety of synthetic plastics and resins. An important example of styrene type monomers in polymerization reaction is in the polymerization of styrene to produce styrene homopolymers and copolymers. In the production of styrene, benzene is alkylated with ethylene in the presence of a suitable inorganic catalyst in order to produce ethylbenzene. The ethylbenzene is dehydrogenated in the presence of an inorganic dehydrogenation catalyst, typically based upon iron and potassium compounds such as ferric oxide and potassium oxide, to produce styrene.

Such dehydrogenation reactions may be carried out in radial flow dehydrogenation reactors. These reactors may take the form of vertically oriented cylindrical reactors having two or more concentric cylindrical shells which can vary in diameter from a few feet to perhaps twenty or thirty feet and which can extend vertically in length to an elevation of more than 100 feet. The ethylbenzene feedstock may be supplied along with a source of heat into the internal flow path of the radial flow reactor. Typically, superheated steam heated to a temperature of perhaps 500-850° C. is introduced into the reactor as a co-feed along with the ethylbenzene feedstock. The steam hydrocarbon mixture flows into the interior tubular member of the reactor and then outwardly through a bed of dehydrogenation catalyst disposed in the annular space between the interior reactor tube and an outer reactor shell. The product containing a mixture of styrene, ethylbenzene as well as hydrogen, steam and water is withdrawn from the top of the radial flow reactor and then passed to a second stage reactor in the reactor system. The input into the second reactor may be passed through a heater and additional steam may be introduced with the input into the second reactor where the feedstock again flows through a catalyst bed in an annular space surrounding the interior reactor tube to effect further dehydrogenation. Additional reactor stages can be employed. Typically, commercial systems employed in the dehydrogenation of ethylbenzene to produce styrene may comprise some 3 or 4 reactors. However, in some cases two series connected reactors are sufficient to achieve the desired styrene product and in other cases single stage reactor systems may be employed.

SUMMARY OF THE INVENTION

In accordance with the present invention there is provided a novel reactor system effective for the dehydrogenation of an alkyl aromatic compound to a corresponding vinyl aromatic compound. The reactor system comprises one or more vertically oriented flow reactors, at least one of which is equipped with a system for the introduction of a catalyst extender into the input of the reactor. The reactor system of the present invention comprises a vertically oriented radial flow reactor comprising inner and outer reactor tubes having perforated wall members which extend longitudily of the reactor and define an annulus in which a porous dehydrogenation catalyst may be located. A supply line extends into the inlet of the radial flow reactor at one end thereof. An injection nozzle comprising a concurrent flow tube extends into the supply line. The concurrent flow tube is defined by an interior chamber and an outer chamber surrounding the interior chamber and extending into the supply line along with the interior chamber. The interior chamber of the injection nozzle is connected to a source of a catalyst rejuvenation material and the outer annular chamber of the injection nozzle is connected to a source of a carrier gas which is effective to carry the extender and disperse the extender within the feedstock flowing into the reactor. The injection nozzle extends into the inlet line by a distance of at least 1 cm and more specifically by a distance of about 1-10 cm. The supply line may be equipped with a rotation vane near the inlet to the reactor which is effective to impart a spiral flow component to fluid flowing through the supply line. The injection nozzle is spaced from the rotating valve, specifically at a location downstream of the rotation vane.

In one embodiment of the invention, the injection nozzle incorporates a spray head which is effective to atomize liquid extender material introduced through the interior chamber of the injection nozzle. The injection nozzle is located downstream of the rotation vane by a distance of 4-20 inches. Alternatively, the injection nozzle may be installed upstream of the rotation vane or some other mixing device. The portion of the supply line in which the injection vane and injection nozzle are located is characterized by an elbow type section having an inlet leg leading into an intermediate transitional section and an outlet leg extending from the transitional section. In some installations the rotation vane is located upstream of the elbow section for the first reactor and upstream of the second elbow for subsequent reactors and the nozzle is located in the inlet leg of the elbow section downstream of the injection vane. The injection nozzle may be located at the portion of the elbow section in which the leg transitions into the intermediate section. The injection nozzle may be positioned at another location that provides for good mixing of the injected material.

In a further aspect of the invention there is provided a dehydrogenation reaction system comprising an initial vertically-oriented radial flow reactor and a subsequent reactor. A flow transfer line extends from the outlet of the initial radial flow reactor to the inlet of the subsequent radial flow reactor. A rotation vane is disposed in the flow transfer line adjacent to the inlet of the reactor. An injection nozzle comprising a coaxial flow tube and annular chamber as described previously extends into the flow transfer line at a location downstream of the rotation vane.

In another embodiment of the invention, the flow transfer line further comprises a second elbow section located downstream of the first recited elbow section. The inlet leg of the second elbow section is connected to the outlet leg of the first recited elbow section. The second elbow section is provided with an intermediate transitional section from which an outlet leg extends. The first and second elbow sections define a u-shaped configuration in which the outlet leg of the second elbow section extends into the inlet of the second radial flow reactor.

In another aspect of the present invention, there is provided a process for the production of styrene by the catalytic dehydrogenation of ethylbenzene. In carrying out this aspect of the invention, an ethylbenzene containing feedstock is supplied into the bottom of a radial flow dehydrogenation reactor characterized by a longitudily extending annular catalyst bed. The radial flow dehydrogenation reactor is operated under temperature and pressure conditions effective to cause dehydrogenation of ethylbenzene to styrene in the presence of the dehydrogenation catalyst. In some installations, the ethylbenzene containing feedstock is introduced into the inlet of the radial flow dehydrogenation reactor through a u-shaped flow path in which the feedstock flows first in a generally vertical direction followed by flow in a generally horizontal direction and by subsequent flow in a general vertical direction opposed to the initial direction of flow. Within the u-shaped flow path, the feedstock is passed over a rotation vane comprising a plurality of turning blades which impart rotational flow to the feedstock within the u-shaped flow path. A catalyst extender is introduced into the feedstock within u-shaped flow path at a location downstream of the rotation vane. The catalyst extender along with the feedstock is flowed into the annular catalyst bed within the radial flow reactor.

In a further embodiment of the invention, the catalyst extender is a potassium salt of a $C_2$-$C_6$ carboxylic acid and the carrier gas is steam, methane or ethane. More specifically, the catalyst extender is potassium acetate and the carrier gas is methane.

DETAILED DESCRIPTION OF THE INVENTION

The present invention may be carried out employing one or more vertically oriented radial flow reactors of any suitable configuration. Such reactors may employ gas-fired or electrical heating systems or they may involve the introduction of a hot fluid such as super heated steam to the reactor along with an ethylbenzene feedstock. A particularly suitable radial flow reactor for use in carrying out the invention incorporates inner and outer reactor tubes defining an annular catalyst bed with a displacement member incorporated within the inner reactor tube in order to direct flow of ethylbenzene into the annular reactor bed in an efficient manner to promote the desired dehydrogenation reaction. A particularly effective radial flow reactor of this type is disclosed in U.S. Pat. No. 5,358,698 to Butler et al and the invention will be described with reference to this type of reactor configuration.

Figure 1:
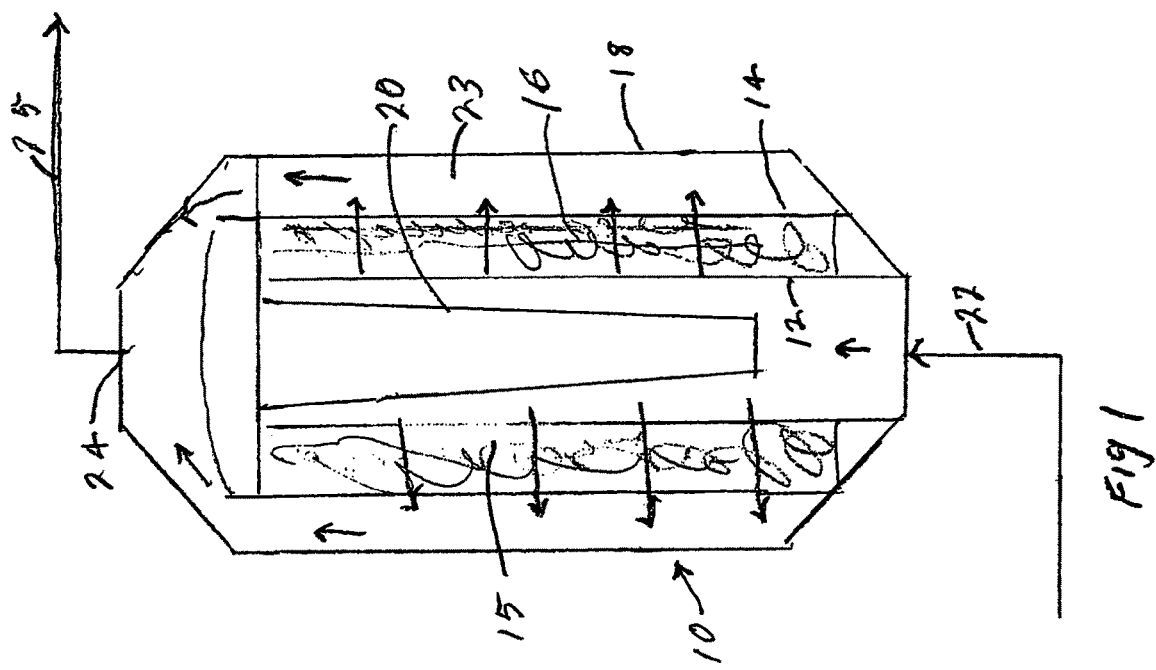
FIG. 1 is a schematic side elevation with parts broken away from a radial flow dehydrogenation reactor of the type employed in the present invention.

Referring initially to FIG. 1, there is shown a side elevation with parts broken away of a vertically-oriented radial flow reactor 10 having an inner reactor cylinder 12 and an outer reactor cylinder 14 which defines an annulus 15 in which a suitable dehydrogenation catalyst 16 is located. An outer reactor shell 18 encompasses the inner and outer reactor cylinders. A displacement cylinder 20 is located within reactor tube 12 and functions to evenly divert flow outwardly through the catalyst bed 16. Inner and outer reactor cylinders 12 and 14 are characterized by perforated wall structures through which fluid reactants and products can flow. The reactor 10 is provided with inlet pipe 22 through which steam and ethylbenzene are supplied into the interior of the reactor. The inlet pipe may be provided with a plurality of flow baffles (not shown) in order to impart a spiraling motion to the feed stream introduced into the reactor. As ethylbenzene flows into the reactor and through catalyst bed 16, it is converted to styrene which flows into the annulus 23 and is withdrawn from the reactor through an outlet 24 at the top of the reactor. The product stream as supplied via line 25 to a suitable processing stage (not shown) for the recovery of styrene or to a downstream reactor connected in series with the reactor 10. For a further description of a suitable dehydrogenation reactor suitable for use in carrying out the present invention, reference is made to the aforementioned U.S. Pat. No. 5,358, 698 to Butler et al, the entire disclosure of which is incorporated herein by reference.

The catalyst employed in the annular catalyst bed 16 may be of any suitable type effective for the catalysis of the ethylbenzene to styrene dehydrogenation reaction. Such catalysts, regardless of their nature, generally undergo a loss of activity, and possibly selectivity, as the dehydrogenation process continues. While the catalyst may be regenerated in place, or more likely replaced with a fresh catalyst, when it reaches a point where unacceptable losses in activity and selectivity are encountered, the effective life of the catalyst can be prolonged by the introduction of a catalyst rejuvenator or extender into the feed stream supplied to the dehydrogenation reactor. Suitable catalyst systems for use in the dehydrogenation of ethylene-benzene, along with the accompanying catalyst extenders, are disclosed in U.S. Pat. No. 6,936, 743 to Butler. As disclosed there, dehydrogenation catalysts which can be employed in styrene production include various inorganic compounds, such as potassium oxide, chromium oxide and iron oxide. As specifically is disclosed in the Butler patent, suitable dehydrogenation catalysts typically contain from about 40-80 wt. % ferric oxide with about 5-30 wt. % potassium oxide and minor amounts of other catalyst promoters. The potassium oxide component is relatively volatile and is vaporized out the catalyst bed during operation of the reactor or migrates and concentrates in the center of the catalyst pellet with the result that the catalyst undergoes an undesirable loss in activity. In order offset the loss of the potassium component, a catalyst rejuvenator extender may be introduced into the reactor in order to extend the life of the catalyst. As disclosed in the Butler patent, suitable catalyst extenders include carboxylic acid potassium salts, such as potassium acetate. The catalyst extenders may be introduced using steam as an effective way to vaporize and heat the catalyst extender. For further description of catalyst systems useful in carrying out the invention, along with rejuvenators therefore, reference is made to the aforementioned U.S. Pat. No. 6,936,743, the entire disclosure which is incorporated herein by reference.

Figure 2:
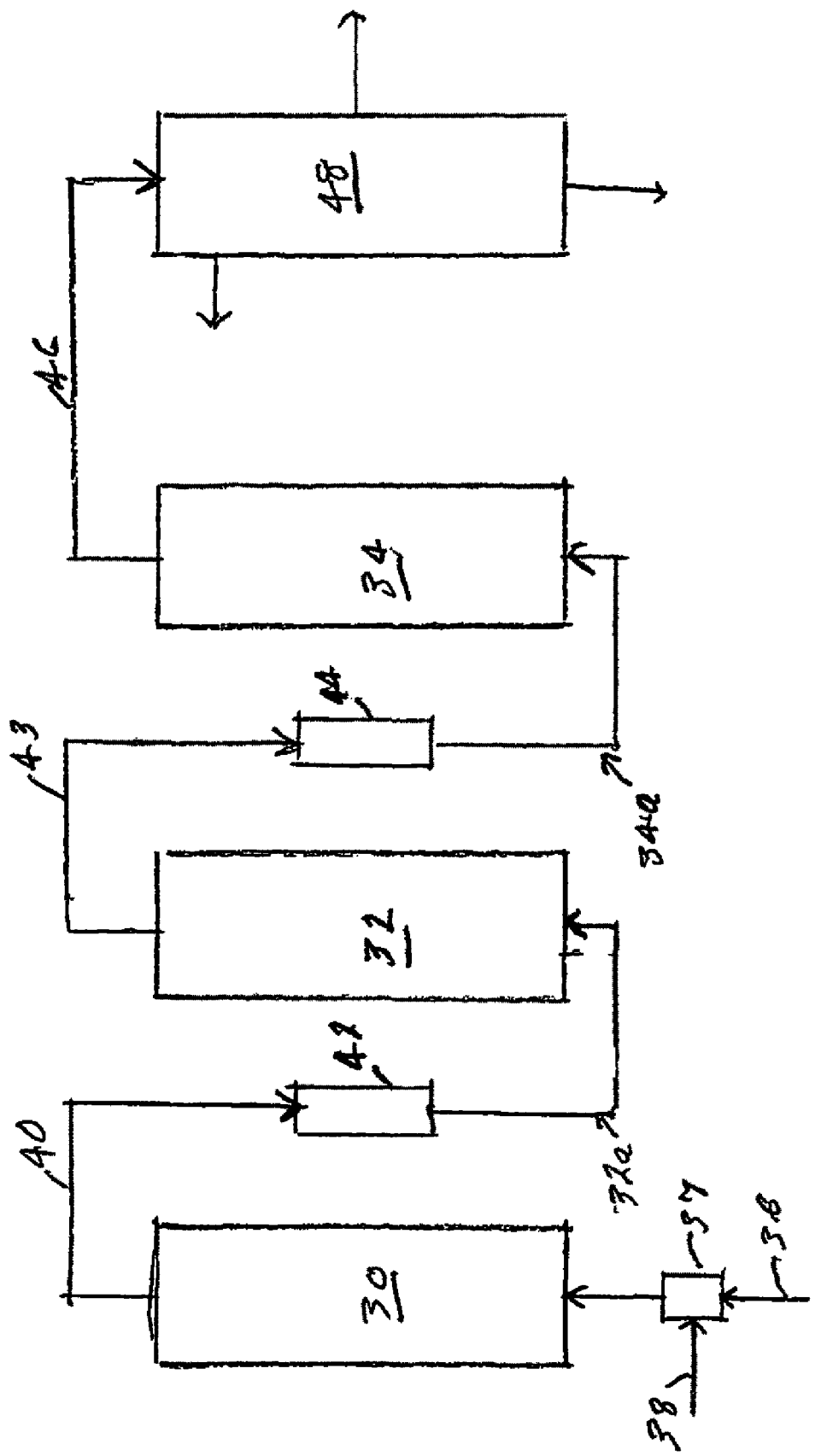
FIG. 2 is a schematic illustration of a reactor system comprising a plurality of radial flow dehydrogenation reactors embodying the present invention.

Referring now to FIG. 2, there is illustrated a reactor system comprising three series connected reactors which may be employed in carrying out the present invention. As shown in FIG. 2, the reactor train comprises a primary reactor 30, a secondary reactor 32, and a final reactor 34. Each of the reactors 30, 32 and 34 may be a reactor of the type disclosed in FIG. 1 employing an internal displacement member to promote the flow of fluid through an annular catalyst bed. As shown in FIG. 2, ethylbenzene is supplied via line 36 to a static mixer 37. Superheated steam is supplied via line 38 to mixer 37. The steam, typically at a temperature of 700-900° C., is mixed with the ethylbenzene at an $H_2O$/ethylbenzene mole ratio of 0.9-12 and then supplied into the bottom of reactor 30 through outlet line 40 (corresponding to line 25 in FIG. 1). The product stream is withdrawn from reactor 30 and supplied through a heat exchanger 42 into the bottom of reactor 32. The product from reactor 32 is in turn supplied via line 43 to a heat exchanger 44 and from there into the bottom of the third stage reactor 34. The outlet from reactor 34 is supplied via line 46 to a separation unit 48 from which styrene, unreacted ethylbenzene, a vent gas and water or steam are recovered for further processing or recycle.

A catalyst rejuvenator, as described previously, may be supplied to one or all of reactors 30, 32, and 34 employing an injection nozzle in accordance with the present invention. Normally in a multi-reactor system of the type depicted in FIG. 2 the injection nozzle, along with an upstream rotation vane, will be located in line 40 close to the inlet to reactor 32 as indicated by location 32A and/or in the inlet line before reactor 34 as indicated by location 34A. The catalyst rejuvenator injection system embodying the present invention can incorporate a rotation vane-injection nozzle system as described with reference to FIG. 3.

Figure 3:
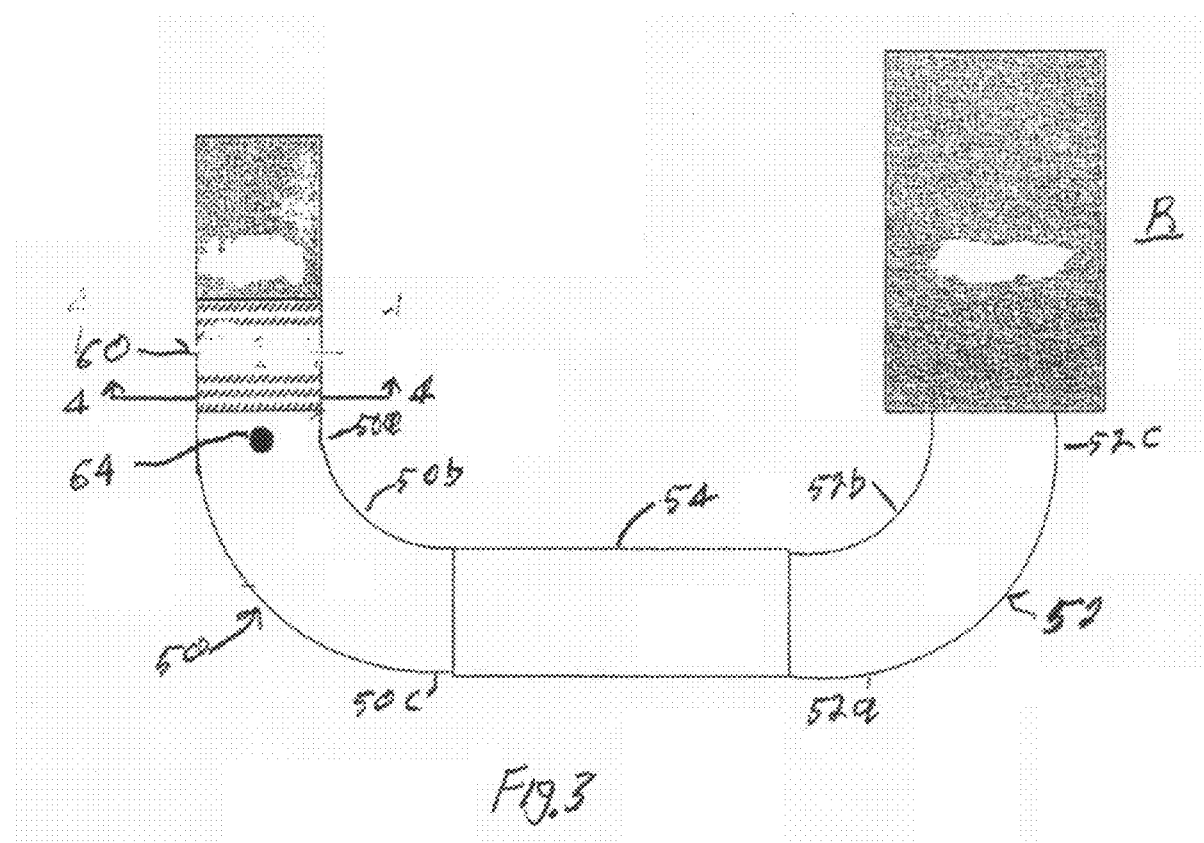
FIG. 3 is an enlarged view of the inlet line of a transfer line extending into a radial flow reactor comprising a rotation vane and an injection nozzle embodying the present invention.

FIG. 3 illustrates the reactor piping extending from an interstage heat exchanger to the bottom of a radial flow reactor R, such as reactor 32 or reactor 34 as shown in FIG. 2. As shown in FIG. 3, the reactor piping involves a u-shaped configuration having a first elbow section 50 and a second elbow section 52 connected through an intermediate tubing section 54. Elbow section 50 comprises an inlet leg 50a, a curved transition section 50b and an outlet leg 50c. Elbow section 52 similarly comprises an inlet leg 52a, an outlet leg 52c and an intermediate transition section 52b.

Figure 4:
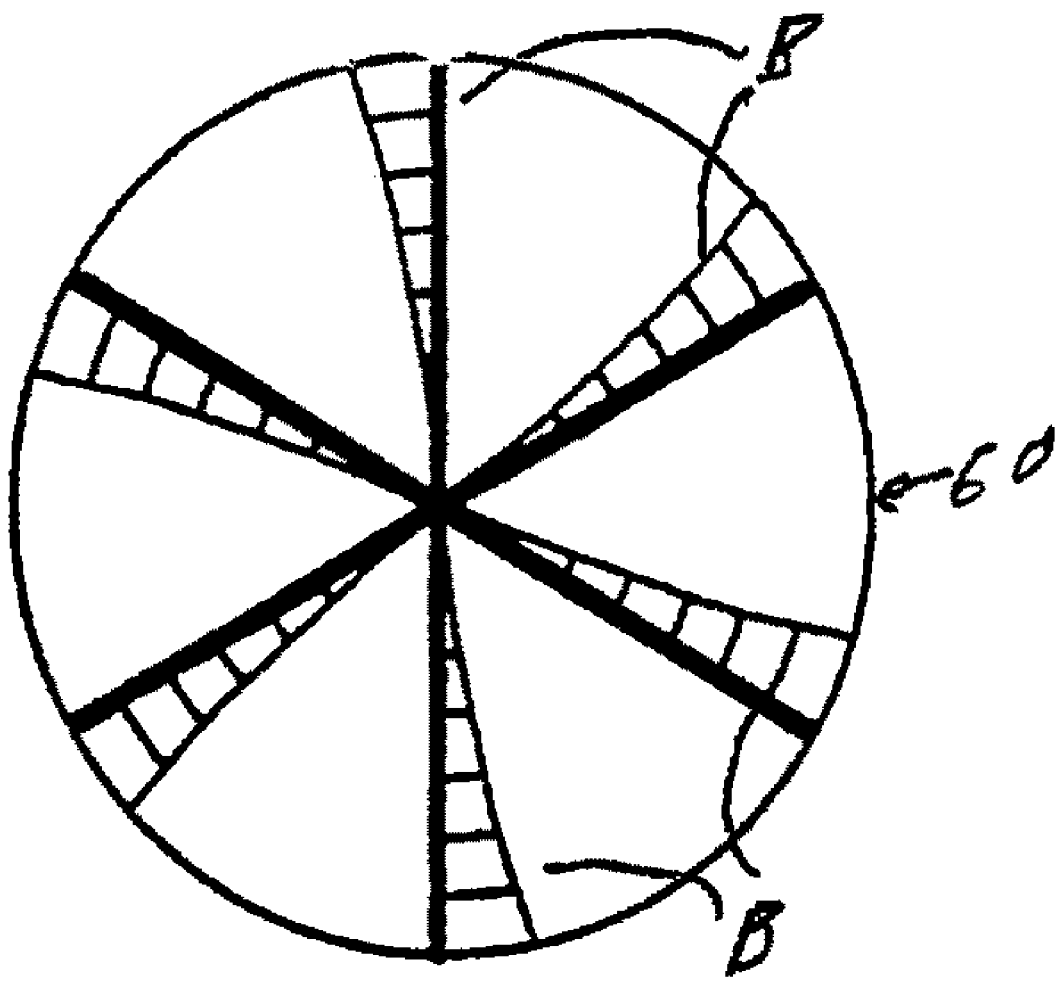
FIG. 4 is a sectional view along line 4-4 of FIG. 3 illustrating the multiple blades in a rotation vane employed in carrying out the invention.

Inlet leg 52 is provided with a vane extension 60 which incorporates a rotation vane of the type designed to impart a spiral flow component to fluid flowing through the reactor piping. Rotation vane 60 may be of any suitable type employing one or more turning blades which impart a spiral flow component to fluid flowing through the rotation vane system. Typically, the rotation vane 60 will comprise an even number of slightly spiraling blades or vanes, for example, 4 to 8 blades. FIG. 4 is a plain sectional view along line 4-4 of FIG. 3 at the bottom of the blades of the rotation vane 60 showing six blades B which are equally spaced about the circumference of rotation vane 60 to impart a spiral flow to fluid flowing through the reactor piping.

Figure 5:
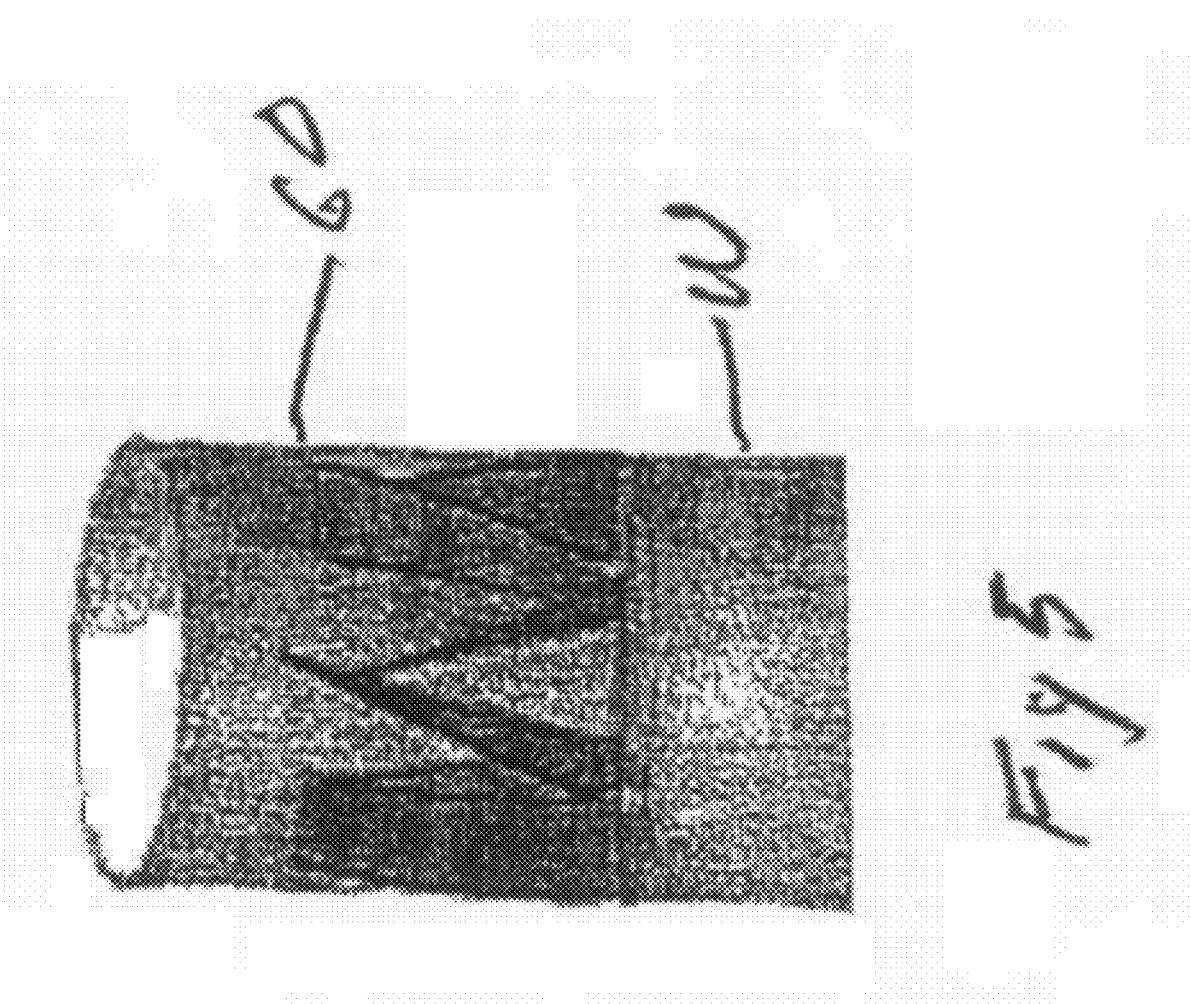
FIG. 5 is a side elevational view with parts broken away showing the blades in the rotation valve vane of FIG. 4.

FIG. 5 is a side elevation of rotation vane 60 with the wall section W shown as a transparency in order to reveal the interior rotation blades B. As can be seen from FIG. 5, the blades B extend longitudily of the rotation vane section by a length that is roughly the same as the diameter of the pipe. For a further description of a suitable rotation vane system which may be employed in carrying out the present invention, reference is made to U.S. Pat. No. 5,323,661 to Cheng, the entire disclosure of which is incorporated herein by reference.

Returning to FIG. 3, the location of an injection nozzle extending into the elbow leg 50 is indicated by reference numeral 64. As indicated, the injection nozzle is located downstream of the rotation vane but in close proximity thereto usually within the range of 4-20", and more particularly 4-10" of the bottom of the rotation vane. In a specific embodiment of the invention, the injection nozzle 64 is located at about 7" below the bottom of the rotation vane 60. In a commercial reactor system employing the present invention with 60" outer diameter (OD) reactor piping, the distance from the center line of elbow leg 50a to the center line of elbow leg 52c is 24 feet. The distance from the bottom of the rotation vane 60 to the center line of reactor piping 54 is 62" and the length of the intermediate pipe section 54 is the length of the tubing section 54 connecting elbows 50 and 52 is 164". In this configuration, the injection point of the injection nozzle indicated by reference numeral 64 is 7" below the bottom of the rotation vane 60. The injection point may vary but it should be located in the inlet leg of the elbow section 54 before the elbow.

Figure 6:
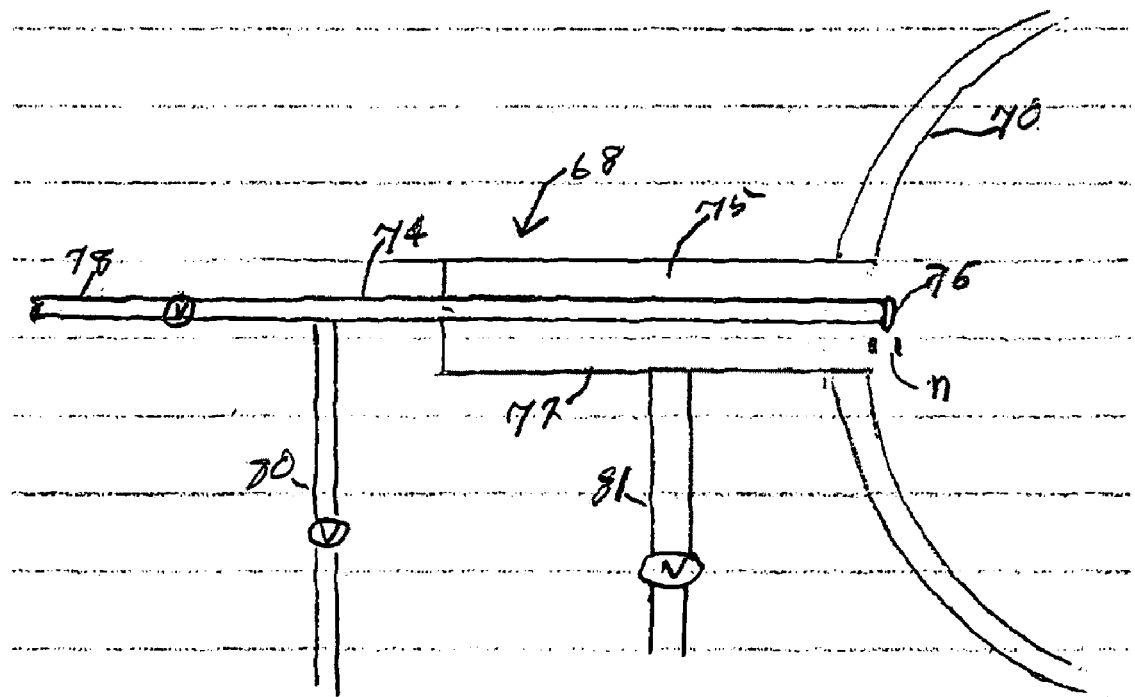
FIG. 6 is a schematic illustration of one type of injection nozzle which may be employed in carrying out the present invention.

The injection nozzle system employed in the present invention will be described with reference to its use in introducing potassium acetate in a methane carrier into the radial flow reactor. However, it will be understood that the operating parameters defined below will be generally applicable to other extender systems. Turning now to FIG. 6, there is illustrated a coaxial injection nozzle 68 which extends into the reactor piping (elbow leg 50a shown in FIG. 3) at a location immediately below the rotation vane. More specifically, and as illustrated in FIG. 6, the wall 70 of the reactor piping is penetrated by an outer nozzle pipe 72 which support a coaxial flow tube 74. The injection tubing 74 and outer pipe 72 define an annular chamber 75 surrounding the injection tubing 74. The injecting tubing penetrates into the interior of the elbow section by a dimension n which may vary from perhaps about 1 to 2 centimeters up to 10 centimeters, and in some cases as much as 50 centimeters. However, experimental work respecting the invention has established that a suitable injection profile can be achieved with an injection nozzle penetration indicated by dimension n of only 1 to 2 centimeters. Somewhat better dispersion can be achieved by increasing the length of dimension n; however, this is offset by abrasion of the injection nozzle. The abrasive action on the injection nozzle of fluid flowing through the reactor piping resulting in structural failure of the nozzle at relatively short time intervals. The introduction of potassium acetate into the reactor pipe at the relatively short intervals of 1 to 2 centimeters can result in undesirable potassium acetate deposits in the reactor tubing. This can be minimized by introducing the potassium acetate solution into the piping at a point well inside the piping of perhaps 25 to 50 centimeters as described above, but this is offset by abrasive destruction of the nozzle as described previously. In order to achieve suitable dispersion of the potassium acetate solution within the reactor feed, a spray head 76 can be incorporated into the tip of the injector tubing in order to disperse the potassium acetate solution in the feed stream into fine droplets of the solution. The use of a spray head on the nozzle enables the dimension n shown in FIG. 6 to be maintained at a relatively small length in order to avoid or at least sharply minimize abrasive action on the nozzle.

Figure 6A:
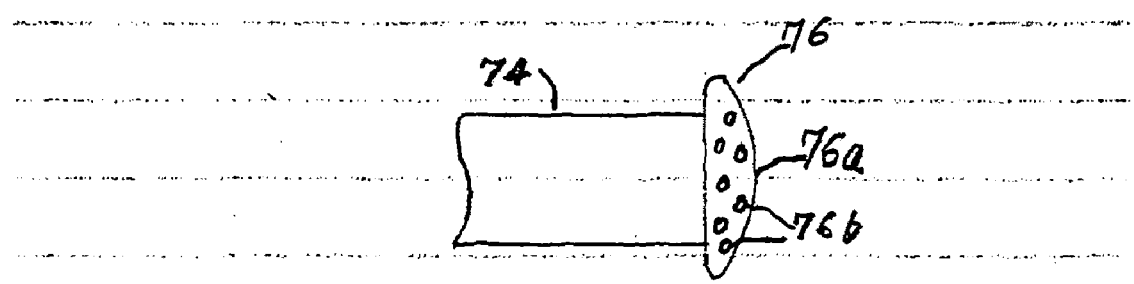
FIG. 6a is an enlarged side elevational view of a portion of the nozzle of FIG. 6.

Spray head 76 can be of any suitable type, such as illustrated in FIG. 6A. FIG. 6A is an enlarged side elevational view of the spray head 76 located at the end of tubing 74. As shown in FIG. 6A, the spray head has a convex outer surface 76a which defines an internal chamber in fluid communication with the end of tubing 74. The convex outer surface 76a is provided with a plurality of small perforations 76b through which the potassium acetate solution is expelled in relatively fine droplets.

Referring further to FIG. 6, the coaxial injection nozzle provides an interior flow tube 74 of about ¼ inch in diameter and an outer tube of about 1 inch in diameter defining the annular chamber 75 surrounding the potassium acetate flow line. Potassium acetate solution is introduced into the interior tubing 74 through a valved feed line 78. Similarly, a methane carrier gas is introduced into the flow tube 74 via valved inlet line 80. Methane is also introduced into the annular chamber 75 through a valved inlet line 81.

At a potassium acetate solution flow rate through line 78 of 0.8 gallons per hour (GPH), the methane flow rate through line 78 into the injection tubing can be about 50 standard cubic feet per hour (SCFH) and the injection of methane through line 81 into the annular chamber 75 also at a rate of about 50 SCFH. The injection of methane (or other suitable inert gas) through line 81 into the annulus 75 performs a dual function in that the carrier gas flow through the annulus cools the interior injection nozzle flow chamber.

Figure 7:
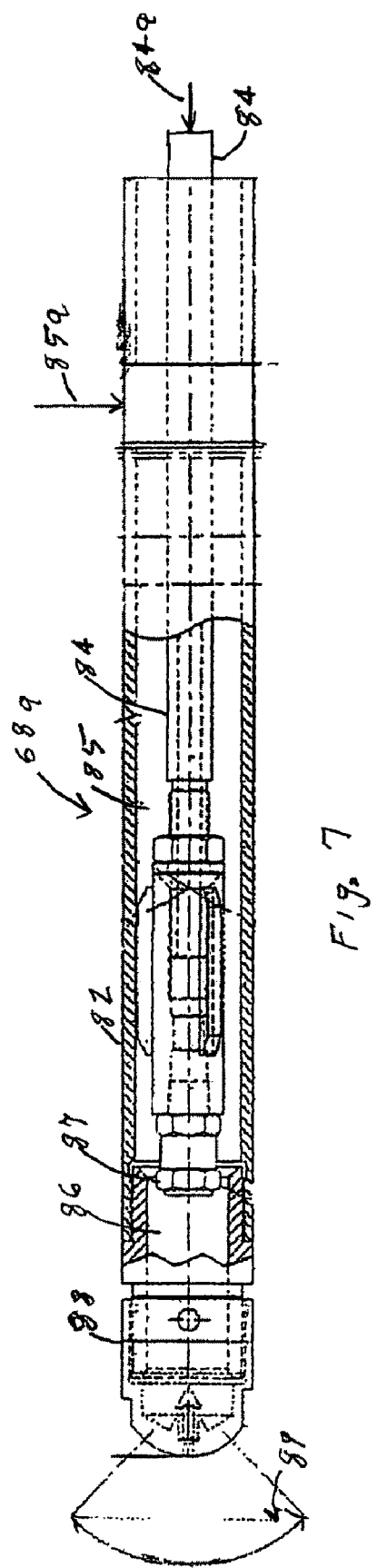
FIG. 7 is a schematic illustration of another embodiment of an injection nozzle which may be used in the present invention.

In another embodiment of the invention, a modified form of an injection nozzle may be employed to supply the catalyst extender to the feed stream in the form of very fine uniform droplets. This embodiment of the invention is illustrated in FIG. 7 which is a side illustration, with parts broken away, similar to FIG. 6, of a modified nozzle 68a. The nozzle of FIG. 7 comprises an outer tubing 82 (corresponding generally to the tubing 72 of FIG. 6) and an inner tubing 84 (corresponding generally to the inner tubing 74 of FIG. 6). The inner and outer tubings 82 and 84 define an annulus 85. The potassium acetate solution, or other catalyst extender, is introduced into tubing 84 through inlet line 84a and an atomizing medium such as methane, steam or nitrogen is introduced into the annular space 85 between tubings 82 and 84 through line 85a. The atomizing medium or other material inert to this process can be used in the annular space of the coaxial feed piping to provide cooling of the injection material to prevent premature evaporation. Premature evaporation of the potassium material may lead to the fouling of the injection pipe. The fluid supply connections to the injection nozzle of FIG. 7 can be similar to those shown for the nozzle of FIG. 6. However, in the modified nozzle 68a, the inner tubing 84 terminates into a mixing chamber 86 through a spray nozzle 87. The natural gas, oxygen or other atomizing medium also flows through annulus 85 into chamber 86. The chamber 86 terminates in a spray cap 88 through which atomized potassium acetate solution or other extender is introduced into the feed stream. The spray cap 88 is configured to provide a 90° spray angle 89 and can extend into the tubular member through which the ethylbenzene is flowing by a distance of about 1-3 cm and provides effective dispersion of the extender. As can be seen from the foregoing description, the operation of the injection nozzle of FIG. 7 is similar to that of FIG. 6 except that rather than introducing the potassium acetate solution directly into the reactor tubing, the potassium acetate solution flows first into the mixing chamber 86 and from there through spray cap 88 into the tubular member associated with the reactor. In operation of the nozzle of FIG. 7, the potassium acetate solution can be introduced into the tubular member 84 at a flow rate of 4-20 gallons per hour. Steam or natural gas can be introduced through line 85a into the annular space 85 under a pressure of 75 psig and the potassium acetate solution can be introduced into the mixing chamber 86 through the spray nozzle 87 at a pressure of 200 psig.

From the foregoing description, it will be recognized that the injection nozzle of FIG. 7 can be employed to introduce the potassium acetate solution or other extender into the feed stream in the form of very fine droplets ranging in size from about 1-100 microns. In simulation studies, droplet sizes ranging from 1 micron to 3 millimeters were carried out in order to determine the effect of the droplet size. Large droplets in the upper end of this range were found to evaporate at a relatively low rates resulting in the formation of solid deposits on the pipe wall near the end of the nozzle. By atomizing the droplets to a size within the range of 1-100 microns, rapid evaporation of the droplets within the time of a few milliseconds substantially reduced and even eliminated the formation of such solid deposits near the nozzle.

While the injection nozzles described above with respect to FIGS. 6 and 7 incorporate coaxial flow tubes which define an annular chamber which surrounds an interior chamber, it will be recognized that other suitable nozzle configurations can be used in carrying out the invention. The nozzle is in any case configured to provide an interior chamber adapted to be connected to a source of a catalyst regeneration material and an outer chamber extending concurrently with the interior chamber and adapted to be connected to a source of a suitable carrier fluid.

As noted previously, an injection nozzle in most cases will be located at a subsequent stage of a multistage reactor system. Thus, considering the location of the injection nozzle at the elbow leading into reactor 32a, as described above, the tubing through which the feed into the reactor flows will be operated at a temperature of 1165° F. The hydrocarbon content flowing through the tubing into the reactor will comprise about 52 wt. % ethylbenzene and about 48 wt. % percent styrene with other hydrocarbon components being neglected. The hydrocarbon and steam flowing from the preceding reactor will provide a steam/hydrocarbon mole ratio of about 9. For a hydrocarbon flow rate of about 192 kilo pounds per hour (klb/hr), the potassium acetate injection rate for a 25% potassium acetate solution (75% water) will be about 20 gallons per day. The methane flow rate into the potassium acetate feed line and into the annulus feed line will be about 50 standard cubic feet per hour in both cases. Operating within these parameters while maintaining the dimension n shown in FIG. 6 at about ½ inch can accomplish the flow of suitable extender into the catalyst bed of the reactor without the deposition of undue amounts of potassium acetate which would lead to unacceptably large solid deposits.

Figure 8:
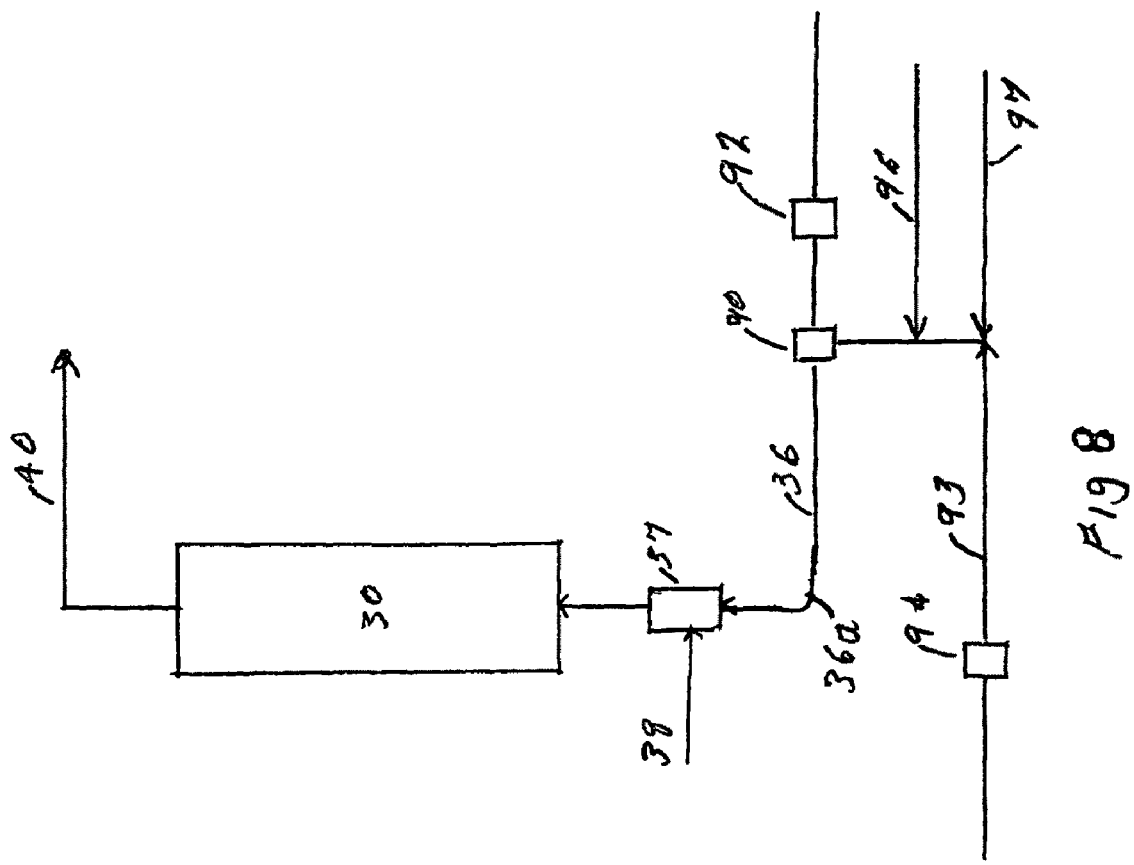
FIG. 8 is a schematic illustration of a reactor system having an injection nozzle in the inlet of the first reactor of a series connected reactor system.

While as described previously with reference to FIG. 3, the injection nozzle is located in the first elbow interposed between reactors, an injection nozzle may also be located in the inlet line leading to the initial reactor 30 shown in FIG. 2. This embodiment of the invention is illustrated in FIG. 8 which is a schematic illustration of the reactor 30 along with the associated mixer 37 supplied with an ethylbenzene feed line 36 and a steam feed line 38. As shown in FIG. 8, an injunction nozzle 90 as described previously with reference to FIG. 6 or FIG. 7 is located in line 36 downstream of a rotation vane 92 corresponding to the rotation vane 60 shown in FIGS. 4 and 5. A potassium acetate solution is supplied to the injection nozzle 90 through a line 93 having a metering pump 94 located therein. In addition a cooling stream which may take the form of natural gas, steam, or nitrogen is supplied to injection nozzle 90 through line 96 and a dilution stream of natural gas, steam or nitrogen is supplied to nozzle 90 through line 97. The line 36 leading to the mixing unit incorporates an elbow section 86a in which the line 36 transitions from a horizontal line in which the injection nozzle is located, to a vertical line leading to the mixer 37 and then to reactor 30.

Having described specific embodiments of the present invention, it will be understood that modifications thereof may be suggested to those skilled in the art, and it is intended to cover all such modifications as fall within the scope of the appended claims.

The invention claimed is:

1. A reactor system effective for dehydrogenation of an alkyl aromatic compound to a corresponding vinyl aromatic compound comprising:
   a) a vertically oriented radial flow reactor comprising an inner reactor tube having a perforated wall and an outer reactor tube having a perforated wall extending longitudinally of said reactor and defining an annulus in which a porous longitudinally extending catalyst bed is located;
   b) a supply line extending into an inlet of said radial flow reactor at one end thereof;
   c) an injection nozzle extending into said supply line, said injection nozzle comprising a concurrent flow tube defined by an interior chamber and an outer chamber extending concurrently with said interior chamber; and
   d) a rotation vane disposed within said supply line adapted to impart a spiral flow component to a fluid flowing through said supply line and wherein said injection nozzle extends into said supply line at a location spaced downstream from said rotation vane;
   wherein no rotation vane is positioned downstream of said injection nozzle.

2. The system of claim 1 wherein said injection nozzle extends into said supply line by a distance of at least 1 cm.

3. The system of claim 2 wherein said injection nozzle extends into said supply line by a distance within the range of 1-10 cm.

4. The system of claim 1 where the interior chamber of said injection nozzle is connected to a source of a catalyst regeneration material and the outer chamber of said injection nozzle is connected to a source of a carrier gas.

5. The system of claim 4 wherein said injection nozzle incorporates a spray head effective to atomize liquid introduced through the interior chamber of said injection nozzle.

6. The system of claim 5 wherein said spray head is effective to atomize said liquid to a droplet size within the range of 1-100 microns.

7. The system of claim 1 wherein said injection nozzle is located downstream of said rotation vane by a distance within the range of 4-20".

8. The system of claim 1 further comprising an elbow section forming part of said supply line and characterized by an inlet leg, extending into a transitional section and an outlet leg extending from said transitional section and wherein said rotation vane is located within the inlet leg of said elbow section.

9. The system of claim 8 wherein said injection nozzle is located in the inlet leg of said elbow section.

10. A reactor system effective for dehydrogenation of an alkyl aromatic compound to a corresponding vinyl aromatic compound comprising:
    a) an initial vertically oriented radial flow reactor comprising an inner reactor tube having a perforated wall and an outer reactor tube having a perforated wall extending longitudinally of said reactor and defining an annulus in which a porous longitudinally extending catalyst bed is located;
    b) a subsequent vertically oriented radial flow reactor comprising an inner reactor tube having a perforated wall and an outer reactor tube having a perforated wall extending longitudinally of said reactor and defining annulus in which a porous longitudinally extending catalyst bed is located;
    c) a flow line extending from the outlet of said initial radial flow reactor to the inlet of said subsequent radial flow reactor;
    d) an injection nozzle extending into said flow line comprising a concurrent flow tube defined by an interior chamber and an outer chamber extending concurrently with said interior chamber; and
    e) a rotation vane disposed within said flow line adjacent to the inlet to said subsequent radial flow reactor, said rotation vane being adapted to impart a spiral flow component to fluid flowing through said flow line and wherein said injection nozzle extends into said flow line at a location spaced from said rotation vane;
    wherein said injection nozzle extends into said flow line at a location downstream of said rotation vane; and
    wherein no rotation vane is positioned downstream of said injection nozzle.

11. The system of claim 10 wherein said injection nozzle extends into said flow line by distance within the range of 1-3 cm.

12. The system of claim 10 where the interior chamber of said injection nozzle is connected to a source of a catalyst regeneration material and the outer chamber of said injection nozzle defines an annular space surrounding said interior chamber and is connected to a source of a carrier gas.

13. The system of claim 10 further comprising an elbow section in the flow transfer line adjacent the inlet of said subsequent radial flow reactor and characterized by an inlet leg, extending into a transitional section and an outlet leg extending from said transitional section and wherein said rotation vane is located within the inlet leg of said elbow section.

14. The system of claim 13 wherein said injection nozzle is located in the inlet leg of said elbow section.

15. The system of claim 14 further comprising a second elbow section located downstream of said first recited elbow section and characterized by an inlet leg connected to the outlet leg of said first recited elbow section and having an outlet leg extending from an intermediate transitional section of said second elbow section whereby said first and second recited elbow sections define a u-shaped configuration, the outlet leg of said second elbow section extending into the inlet of said second radial flow reactor.

* * * * *